United States Patent
Castro

(10) Patent No.: US 8,333,768 B2
(45) Date of Patent: Dec. 18, 2012

(54) METHOD AND APPARATUS FOR NONSURGICAL CORRECTION OF CHEST WALL DEFORMITIES

(75) Inventor: Alejandro Castro, N. Bay Village, FL (US)

(73) Assignee: William Gallo, Miami, FL (US)

( * ) Notice: Subject to any disclaimer, the term of this patent is extended or adjusted under 35 U.S.C. 154(b) by 292 days.

(21) Appl. No.: 12/655,874

(22) Filed: Jan. 8, 2010

(65) Prior Publication Data

US 2011/0172576 A1    Jul. 14, 2011

(51) Int. Cl.
  *A61F 2/30*    (2006.01)
  *A61F 2/46*    (2006.01)
  *A61F 5/00*    (2006.01)

(52) U.S. Cl. ............. 606/86 R; 602/19; 606/60; 606/99

(58) Field of Classification Search ........... 606/86 R, 606/60, 99, 330; 602/19
  See application file for complete search history.

(56) References Cited

U.S. PATENT DOCUMENTS

| | | | |
|---|---|---|---|
| 2,800,902 A | 7/1957 | Wiltrout | |
| 3,598,114 A | 8/1971 | Lewis | |
| 6,024,759 A | 2/2000 | Nuss | |
| 7,229,422 B2 | 6/2007 | Klobe | |
| 8,043,290 B2 * | 10/2011 | Harrison et al. | 606/60 |
| 2006/0074448 A1 | 4/2006 | Harrison | |

FOREIGN PATENT DOCUMENTS

WO    WO 2004028412 A1 *    4/2004
WO    WO 2005055844 A1 *    6/2005

OTHER PUBLICATIONS

"A 10-Year Review of a Minimally Invasive Technique for the Correction of Pectus Excavatum" Nuss et al. Journal of Pediatric Surgery, vol. 33, No. 4 Apr. 1998: pp. 542-552.*

Sydney A. Haje, preliminary results of orthotic treatment of pectus deformities in children, journal of pediatric orthepedics, 1992, 12: p. 795-800, Raven Press LTD, NY.

* cited by examiner

Primary Examiner — Kim M Lewis

(57) ABSTRACT

One embodiment of a method and apparatus for the correction of pectus excavatum, having two arch shaped braces (22), made of a rigid durable material, and connected by a flexible belt (42 and 34), each half having the ability of applying positive pressure (26) to the flared ribs caused by the condition. Positive pressure is to be applied to the ribs while a suction cup or other device simultaneously pulls or pushes the sternum to a natural position. Other embodiments are described and shown.

2 Claims, 5 Drawing Sheets

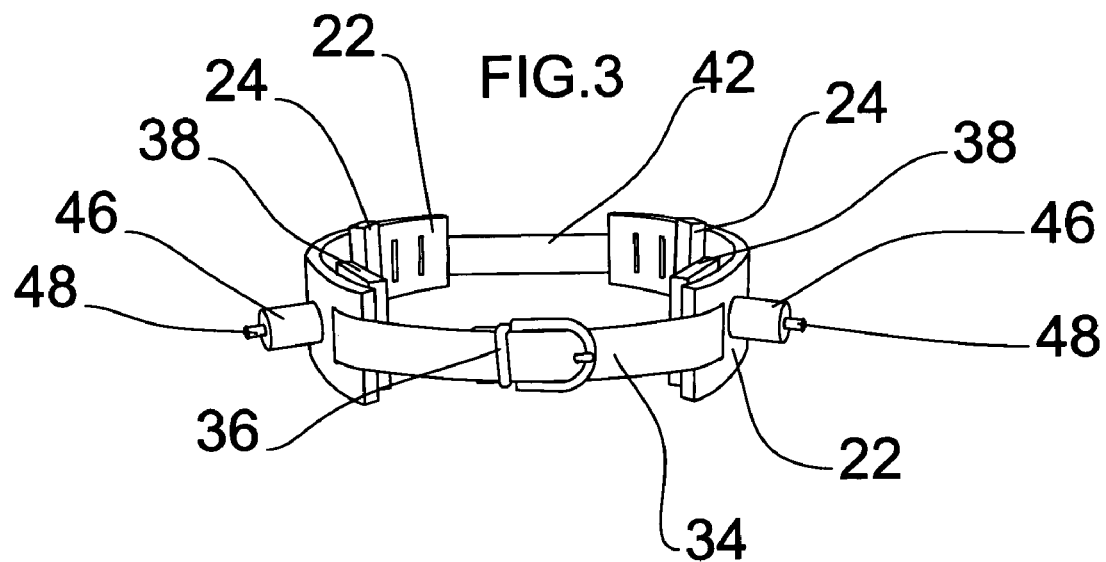
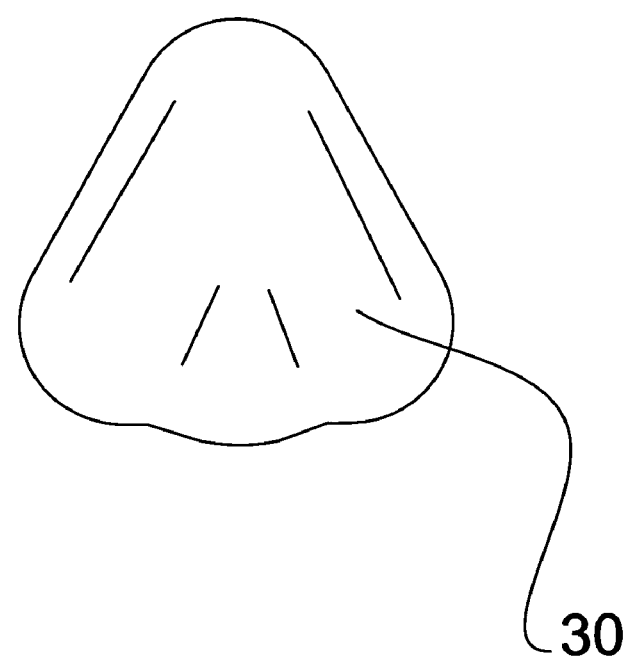

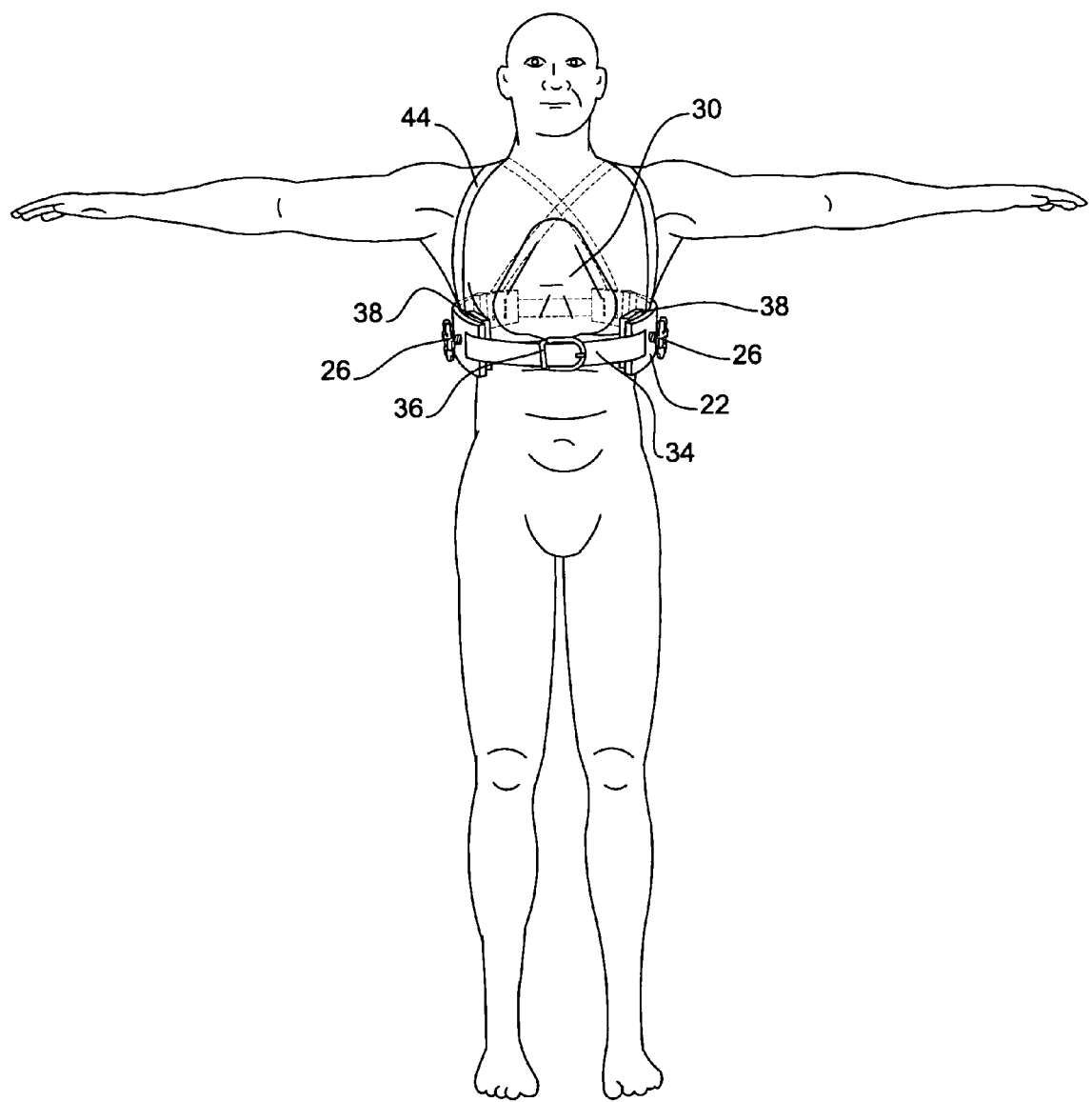

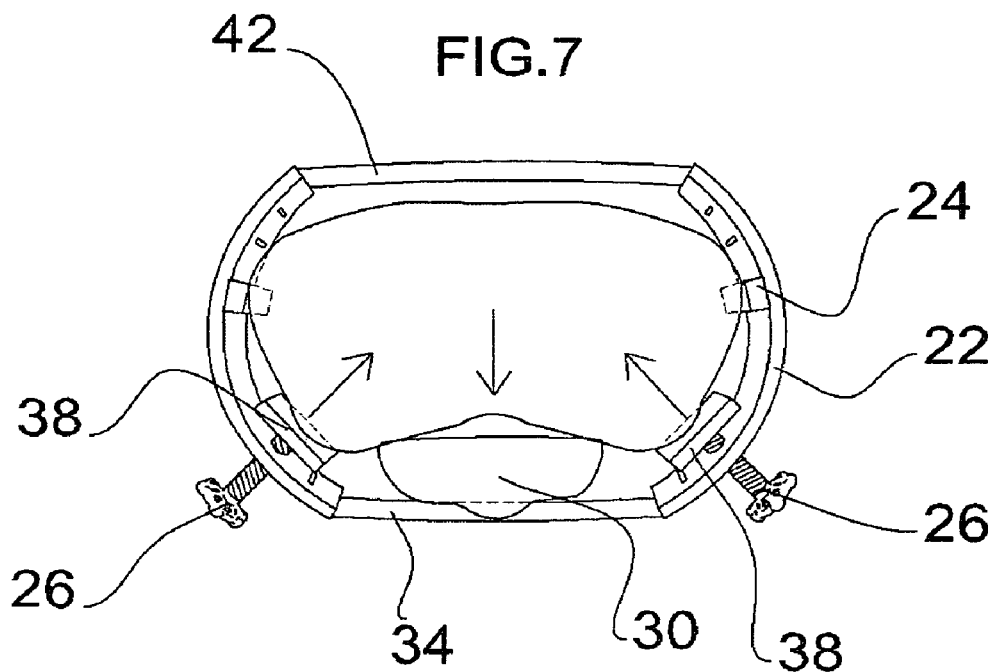
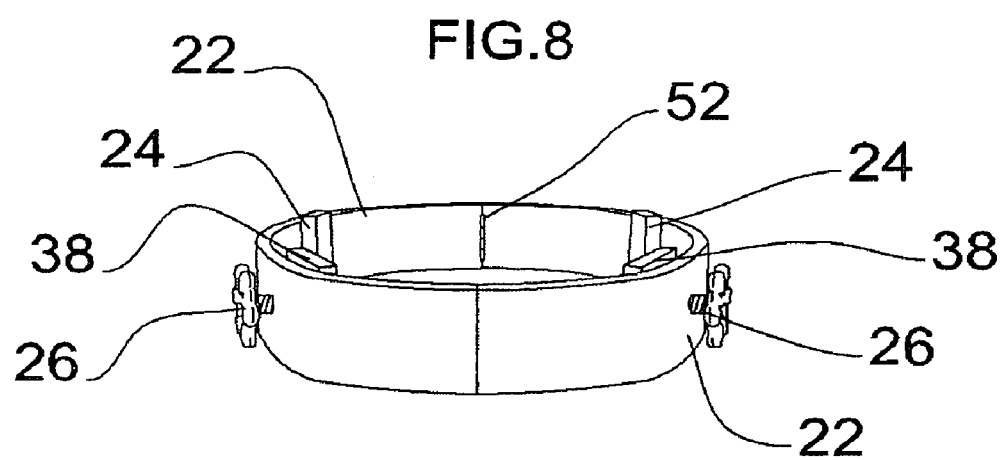

METHOD AND APPARATUS FOR NONSURGICAL CORRECTION OF CHEST WALL DEFORMITIES

BACKGROUND—PRIOR ART

The following is a tabulation of some prior art that presently appears relevant:

U.S. Patents

| Pat. No. | Kind Code | Issue Date | Patentee |
|---|---|---|---|
| 7,229,422 | B2 | Jun. 12, 2007 | Klobe |
| 6,024,759 | A | Feb. 15, 2000 | Nuss |
| 2,800,902 | | Jul. 30, 1957 | Wiltrout |
| 3,598,114 | | Aug. 10, 1971 | Lewis |

U.S. Patent Application Publications

| Publication Number | Kind Code | Publ. Date | Applicant |
|---|---|---|---|
| 2006/0,074,448 | A1 | Apr. 6, 2006 | Harrison |

Nonpatent Literature Documents

Journal of Pediatric Orthopedics—*Preliminary Results of Orthotic Treatment of Pectus Deformities in Children and Adolescents* [Sydney A. Haje, M.D. and J. Richard Bowen M.D.] 1992 Raven Press Ltd., New York.

It has been estimated that Pectus Excavatum affects up to 1 percent of the world's population, making it the most common of the chest wall deformities. This deformity can effect major organs and impair breathing and heart function.

In the 1940's the Ravitch procedure was developed, this involved removal of the ends of the ribs as they attach to the sternum in the depressed area. The lining membrane around the rib is left in place. The sternum is then broken horizontally at the point where it turns downward and is straightened out. It is held in this position using stitches, the adjacent ribs and usually a metal bar or strut that goes under the sternum to keep it in an outward position. This all takes place under the skin, and is not without its complications. Side effects can include post operative pain, infection, and fluid collection under the skin. In addition the ribs must grow back for complete chest wall stability to occur.

The Nuss procedure (U.S. Pat. No. 6,024,759) has become more popular over the last 10 years. This operation has been described generally as "minimally invasive." An incision is made on each side of the chest wall. A bar is bent into the desired shape of the chest wall. A large surgical clamp is passed through one side of the chest, under the sternum and out the other side. The bar is pulled through using the clamp with the curve of the bar in the opposite direction. It then is flipped over and, in the process, bends the sternum outward, stretching the ribs as it does so. The bar is left in place for several months or years. A comparison of the Nuss "minimally invasive" procedure and the Ravitch procedure, published in the *Journal of Pediatric Surgery*, shows no advantage for the Nuss procedure. The likelihood of recurrence of the chest deformity following the Nuss procedure has been slightly greater than with the Ravitch procedure. There have been ongoing modifications of the Nuss procedure to improve the results and eliminate complications, some of which have been life threatening.

Recently the use of a vacuum bell (U.S. Pat. No. 7,229,422) for the elevation of the sternum has become popular, though a similar device was used as early as 1910 by Lange. The suction cup is applied over the depressed area of the chest. Air is removed from the chamber creating a vacuum which lifts the sternum temporarily. After several hours the chest returns to its original position. The use of a suction device alone has proven ineffective in maintaining long term results.

Lastly, the dynamic chest compressor, introduced by Haje, involves a brace that is applied to the lower chest. Pressure is applied to front side of the rib cage. The brace must be worn for a good portion of the day in order to be effective. A. Dynamic Chest Compressor (DCC) brace by itself is useless unless it is made correctly and worn for the correct daily number of hours according to each period of the treatment, and applied along with an appropriate program of exercises. In addition, the Dynamic Chest Compressor (DCC) is a device that must be manufactured according to each individual deformity for successful treatment.

SUMMARY

In accordance with one embodiment, a means of pushing the flared ribs back into their normal position, while a suction cup or other device pulls or pushes the sternum upward into its natural position. s Advantages Thus several advantages of one or more aspects are as follows: to provide a safe means of correcting the condition known as pectus excavatum without having to undergo a risky surgical procedure, to provide a means for the correction of the flared ribs associated with pectus excavatum, to provide a means of nonsurgical correction that does not involve hours of strenuous exercise per day, to provide a means of correction that does not involve the wearing of a brace for the majority of the day, to provide a brace that is one size fits all and does not have to be specially tailored to each individual. I have found that the depression of the sternum is caused by an overgrowth of the flared ribs. In order to correct the position of the sternum the position of the ribs must be addressed. Other advantages of one or more aspects are to address the funnel in the chest by simultaneously addressing the flared ribs, thus permanently correcting the position of both the sternum and the ribs. These and other advantages of one or more aspects will become apparent from a consideration of the ensuing description and accompanying drawings.

DRAWINGS—FIGURES

FIG. 3 shows a perspective view of an embodiment of the rib compressor.

FIG. 4 shows a top plan view of an embodiment of the suction device.

FIG. 6 shows a perspective view of an embodiment of my invention, a rib compressor with shoulder straps and suction device applied to the human form.

FIG. 7 shows a perspective view of an embodiment of my invention taken from the top as applied to a sectional view of a body suffering from pectus excavatum. Arrows depict the forces being applied to the sternum and flared ribs.

FIG. 8 shows a perspective view of an embodiment of my invention.

DRAWINGS

Reference Numerals

| | |
|---|---|
| 22. | Brace |
| 24. | Spacer |
| 26. | Bolt |
| 27. | Clutch mechanism |
| 28. | Support Ribs |
| 29. | Notched extrusion |
| 30. | Suction Cup |
| 32. | Tube Nozzle |
| 34. | Front Belt |
| 36. | Belt Buckle |
| 38. | Plate |
| 40. | Pad |
| 42. | Rear Belt |
| 44. | Shoulder Strap |
| 46. | Piston Chamber |
| 48. | Tube Nozzle |
| 50. | Piston |
| 52. | Hinge |

DETAILED DESCRIPTION

First Embodiment—FIGS. 1, 2, 4, 5a, 6 and 7

Figure 1:
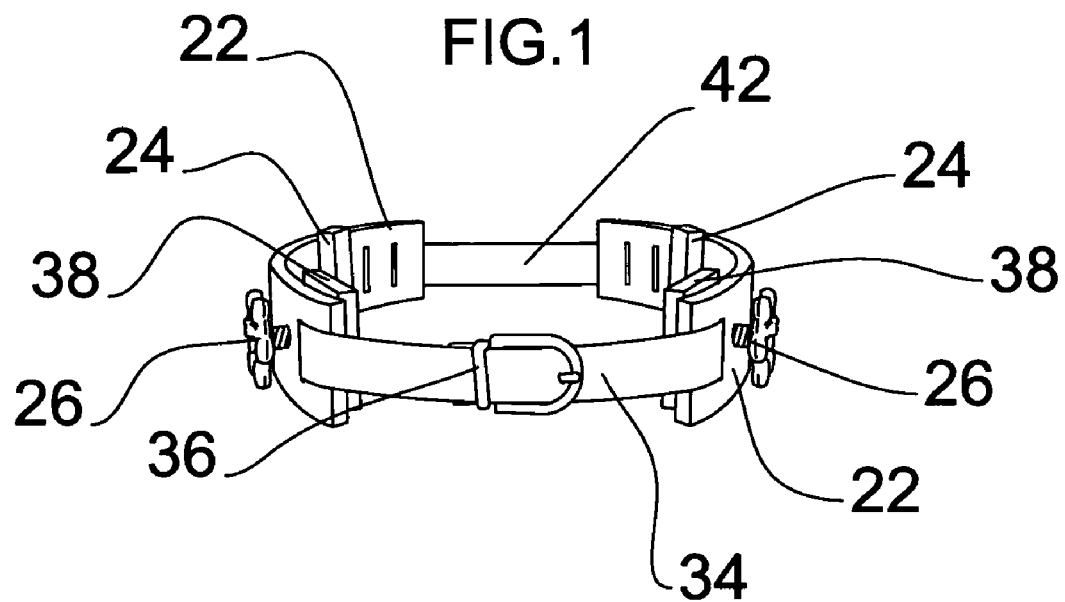
FIG. 1 shows a perspective view of an embodiment of the rib compressor.

FIGS. 1, 6 and 7 show perspective views of the rib compressor of the 1$^{st}$ embodiment from front and top. The rib compressor has two arch shaped braces 22 of equal length which face each other at opposite ends. I contemplate that the braces 22 of this embodiment be made of polyurethane or nylon, but other materials are also suitable. Both Braces 22 are connected to each other by a belt at the rear 42 and a belt at the front 34. The front belt 34 of this embodiment being made of two separate lengths of material having a belt buckle 36 to secure both together, best shown in FIG. 1. I contemplate that the belts 42 and 34 can be made of Leather or canvas but other materials are also suitable.

Connected to brace 22 is a spacer 24, best shown in FIG. 7, attached by virtue either of the extrusion of liquid plastic (which will form the body of the brace) or the application of heat or adhesive upon the side of the spacer.

Each brace 22 has a bolt 26 which secures to the brace 22 by virtue of a threaded opening in the brace to accept the threaded bolt, being best depicted in FIG. 7. The bolt 26 having a hand grip and a calibrated clutch mechanism 27 is connected to a plate 38 (depicted in FIG. 5a) by means of a notched extrusion 29 in the bolt, although other means of attachment would be adequate. The base plate 38, being made of polyurethane or other suitable material, is connected to a pad 40 that can be made of liquid rubber, foam or other soft material that would provide adequate padding. I contemplate the pad 46 can be attached to plate 38 by the application of heat or adhesive on either side.

Figure 2:
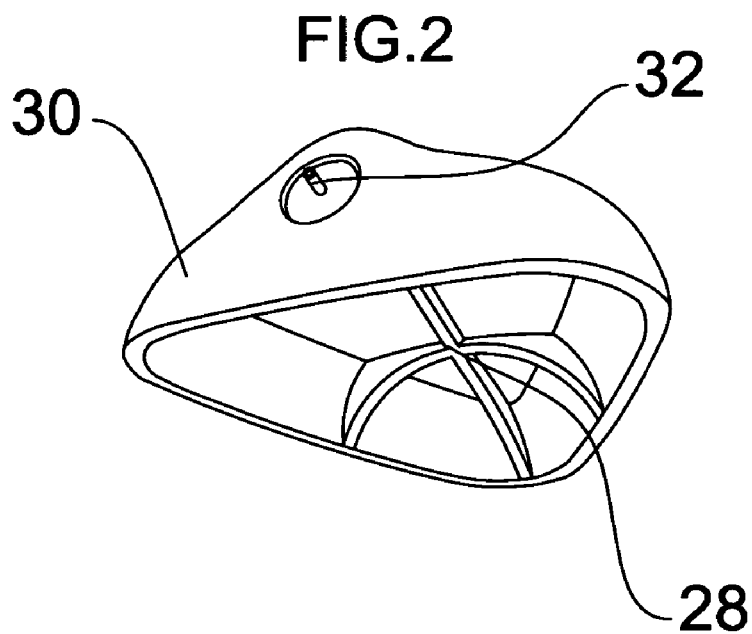
FIG. 2 shows a perspective view of the suction device depicting inside chamber and ribs.

FIGS. 2, 4, 6 and 7 depict a suction device 30 of an embodiment from various perspectives. The suction device 30 having a three sided triangular shape (when viewed from the top as depicted in FIG. 4) with rounded edges can be constructed of rubber or other pliable air tight material. Attached to the suction device 30 is a rib system 28 depicted in FIG. 2. I presently contemplate that the ribs 28 can be made of polyurethane or nylon; however other materials are also suitable. The ribs 28 are attached to the suction device 30 by either embedment in the liquid rubber (which will form the body of the suction device), an adhesive or other means. Attached to the suction device 30 is a tube nozzle 32, as depicted in FIG. 2. The tube nozzle, having a circular base, is attached to the suction device by embedment in the liquid rubber that will form the body of the suction device 30. The tube nozzle can be constructed of plastic, copper or other suitable material. s Operation—First Embodiment—FIGS. 6 and 7

The rib compressor assembly and suction device of this embodiment are to be used in unison; however they can also be used separately. As shown in FIGS. 6 and 7, the rib compressor is placed so that the pads 40 are in contact with the flared ribs, creating a surface transfer area. The belt is tightened and the buckle secured so as to place pressure on the ribs while maintaining the assembly in place. The suction device 30 is placed so as to cover the depression at the sternum. Once adequate contact has been made between the patient's skin and the suction device so as to maintain an air tight seal, air is removed from the suction chamber via the nozzle 32 by a hand pump or other device. The sternum is lifted by the negative forces in the vacuum and in most cases the patients flared ribs flare further outward. Once the sternum is raised adequately, the Rib Compressor bolts 26 are tightened so as to compress the flared ribs inward into the desired position. The forces applied by both the suction and the rib compression devices are depicted in FIG. 7. The correction of the flared ribs is crucial to the correction of the depression in the chest, as I have discovered, the inwardly sunken sternum is caused by the position of the outwardly flared ribs.

The front and rear belts 34 and 42 are adjustable, allowing the patient to adjust the brace to fit to their own body, thus eliminating the need for a custom manufactured brace.

The bolts 26 have a clutch mechanism 27 that can be calibrated as needed to meet each individual patients needs at different phases of their treatment. This allows a means for the patient to apply the prescribed amount of pressure to the ribs. s Description—Alternative—Embodiment—FIGS. 3, 5b and 5c

There are various possibilities with regard to the means of exerting pressure to the flared ribs. FIG. 3 shows a front perspective view of an embodiment with the braces 22 having piston chambers 46 attached. I presently contemplate that the piston chamber 46 can be attached to the brace 22 by means of an extrusion of the liquid plastic which forms the brace, although other means of attachment may be adequate.

Figure 5A:
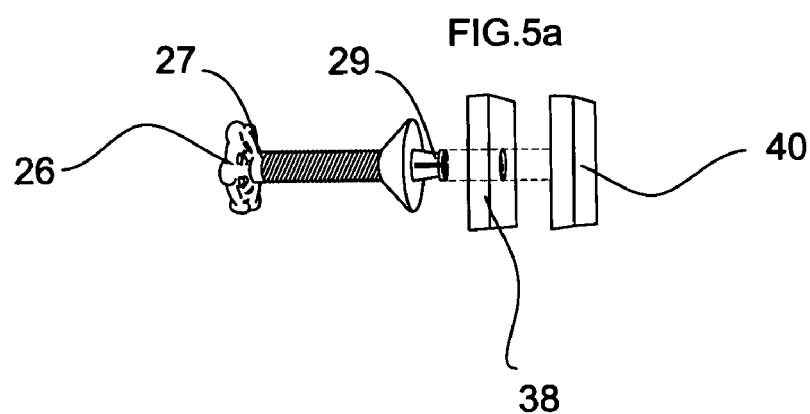
FIG. 5a shows an exploded view of the bolt and base plate assembly.
Figure 5B:
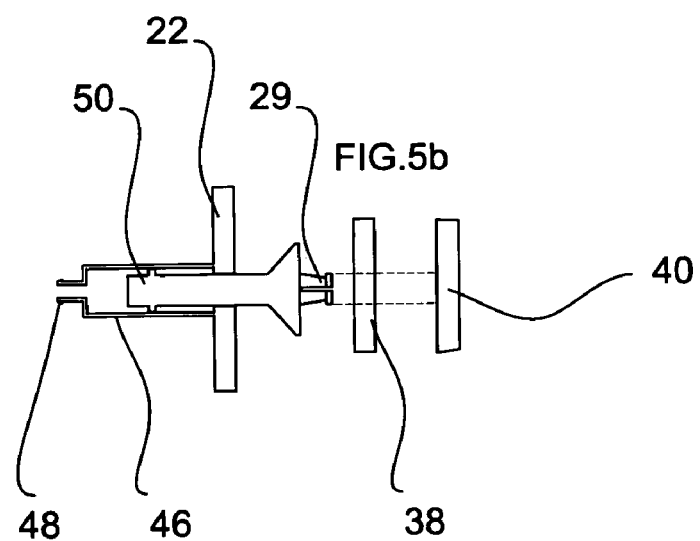
FIG. 5b shows a sectional view of an alternate embodiment of the compression mechanism.
Figure 5C:
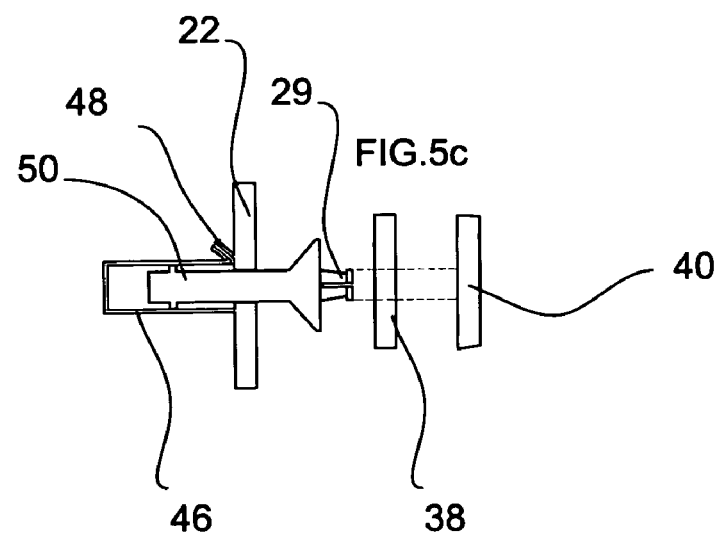
FIG. 5c shows a sectional view of an alternate embodiment of the compression mechanism.

The piston chamber 46 being best depicted in FIGS. 5b and 5c has one piston 50, the piston passes through an opening in the brace 22 and has plate 38 attached. The piston chamber has a nozzle 48 attached at either the rear of the chamber as shown in FIG. 5b or toward the front of the brace as shown in FIG. 5c.

There are also various possibilities with regard to the brace. FIG. 8 depicts a front perspective of any embodiment having extended versions of the braces 22. The braces are connected at the rear of this embodiment by a hinge 52. s Operation—Alternative—Embodiment—FIGS. 5b, 5c 6 and 8.

FIG. 5b depicts a sectional view of an embodiment of the compression mechanism having the nozzle 48 at the rear of the chamber 46; piston 50 would be pushed out by virtue of a hand pump or other device pumping gas or liquid into the chamber. The piston would then move thru the brace 22 and exert added pressure to the patient's ribs via a surface transfer area.

FIG. 5c depicts a sectional view of an embodiment of the compression mechanism having the nozzle 48 toward the front of the chamber 46 adjacent to the brace 22. Piston 50 would be pulled in, by the removal of gas or liquid thru the brace 22 and exert the required pressure to the patients ribs.

FIG. 8 depicts a front perspective view of an embodiment having a hinge 52 at the rear providing a means of opening and closing the brace for access around the patients body. s
Conclusion, Ramification, and Scope Accordingly the reader will see that, according to one embodiment of the invention, I have provided a practical means of permanently correcting the chest wall deformity typically referred to as pectus excavatum (also known by other names such as funnel and sunken chest). In addition to the correction of the sternum, the reader will find that according to one embodiment, the displaced ribs typically associated with pectus excavatum are also provided with a means of correction.

While the above description contains many specificities these should not be construed as limitations on the scope of any embodiment, but as exemplifications of various embodiments thereof. Many other ramifications and variations are possible within the teachings of the various embodiments. For example, the means of compressing the ribs inward could be an inflatable flexible envelope that when inflated would expand and place the required pressure on the ribs. Additionally, the rib compressor may, on occasion, be used alone in order to only treat the outwardly deformed ribs of a patient.

Thus this scope should be determined by the appended claims and their legal equivalents, and not by the examples given.

The invention claimed is:

1. A new method for the correction of pectus excavatum and/or flared ribs comprising:
   a. elevating a sternum of a patient to a desired position;
   b. compressing a patient's flared ribs back into a desired position while the sternum is being raised, whereby overtime the sternum will accept the desired position by virtue of the ribs new position.

2. The method of claim 1, wherein the sternum is raised by applying negative pressure above the sternum.

* * * * *